(12) United States Patent
Li et al.

(10) Patent No.: US 8,581,238 B2
(45) Date of Patent: Nov. 12, 2013

(54) DITHIENOTHIOPHENE DERIVATIVES

(75) Inventors: Chang Ming Li, Singapore (SG); Jun Li, Singapore (SG); Beng Ong, Singapore (SG); Qin Fang, Singapore (SG)

(73) Assignee: Nanyang Technological University, Singapore (SG)

( * ) Notice: Subject to any disclaimer, the term of this patent is extended or adjusted under 35 U.S.C. 154(b) by 585 days.

(21) Appl. No.: 12/918,691

(22) PCT Filed: Feb. 19, 2009

(86) PCT No.: PCT/SG2009/000057
§ 371 (c)(1),
(2), (4) Date: Aug. 20, 2010

(87) PCT Pub. No.: WO2009/105041
PCT Pub. Date: Aug. 27, 2009

(65) Prior Publication Data
US 2010/0327273 A1 Dec. 30, 2010

Related U.S. Application Data (60) Provisional application No. 61/030,479, filed on Feb. 21, 2008.

(51) Int. Cl.
*H01L 35/24* (2006.01)
(52) U.S. Cl.
USPC .................................. 257/40; 257/E51.001

(58) Field of Classification Search
USPC ............................................. 257/40, E51.001
See application file for complete search history.

(56) References Cited

PUBLICATIONS

J. Frey et al., "Improved Synthesis of Dithieno[3,2-b:2',3'-d]Thiophene (DTT) and Derivatives for Cross Coupling," *Chem. Commun.*, pp. 2424-2425, 2002.
J. Li et al., "High-Performance Thin-Film Transistors from Solution-Processed Dithienothiophene Polymer Semiconductor Nanoparticles," *Chemistry of Materials*, vol. 20, No. 6, pp. 2057-2059, Feb. 23, 2008.
Q. Bao et al., "Direct Observation and Analysis of Annealing-Induced Microstructure at Interface and Its Effect on Performance Improvement of Organic Thin Film Transistors," *The Journal of Physical Chemistry B*, vol. 112, pp. 12270-12278, Sep. 5, 2008.

*Primary Examiner* — Anthony Ho
(74) *Attorney, Agent, or Firm* — Dickstein Shapiro LLP (57) ABSTRACT

An organic compound represented by the following general formula (I) wherein n is an integer from 1 to 500, inclusive, and R1 and R2 are each independently a moiety having an atom length of from about 8 atoms to about 20 atoms.

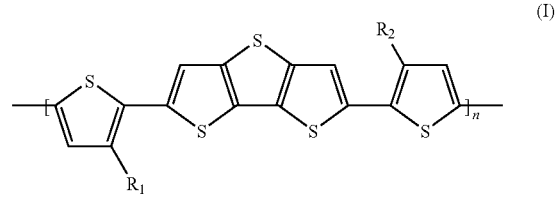

12 Claims, 6 Drawing Sheets

DITHIENOTHIOPHENE DERIVATIVES

This application claims the benefit of U.S. Provisional Application No. 61/030,479, filed on Feb. 21, 2008.

BACKGROUND OF THE INVENTION

The present invention relates generally to organic compounds for semiconductor applications.

Organic materials offer a low-cost alternative to traditional inorganic materials such as inorganic silicon and gallium arsenide that are presently being used in electronic device manufacturing. Additionally, their compatibility with plastic substrates renders them ideal for compact, lightweight, mechanically flexible, and structurally inspiring electronic device designs. However, currently known solution-processable semi-conducting polymers typically afford poor transistor properties such as, for example, low charge carrier mobility and low current on/off ratio, when such semiconductors are deposited in air. Thus, it would be desirable to have an organic semiconductor material that retains desirable semiconductor properties when processed under ambient conditions.

SUMMARY OF THE INVENTION

The invention provides compounds that are particularly useful when employed as semiconductors or charge transport materials in electronic devices such as organic field effect transistors (OFETs), organic light emitting diodes (OLEDs), and organic photovoltaic diodes.

In a first aspect, the invention provides a compound of formula (I):

wherein
n is an integer from 1 to 500, inclusive; and
R1 and R2 are each independently a moiety having an atom length of from about 8 atoms to about 20 atoms.

In some examples, one or both of R1 and R2 may have an atom length of from about 10 atoms to about 16 atoms. In some examples, one or both of R1 and R2 may have an atom length of about 12 atoms.

In the above formula, one or both of R1 and R2 may independently comprise one or more of a group comprising: an alkyl, an alkenyl, an alkynyl, an amine, a carbonyl, an ester, a carbonate ester, an ether, a sulphide, an organosilane and a thioate. In some examples, one or both of R1 and R2 may comprise a straight chained alkyl. In one embodiment, both R1 and R2 are dodecyl.

In some examples, n may be an integer from 4 to 40, inclusive.

The compounds of formula (I) have suitably long sidechains. This improves solution processability. Additionally, the compounds of formula (I) have substantial structural regularity. Advantageously, this induces and facilitates molecular self-assembly. Additionally, due to proper control of its extended p-conjugation, an excellent balance is struck between transistor functionality and oxidative doping stability. This extends the life span of a device. Further advantages include high charge carrier mobility and high current on/off ratio in air.

In another aspect, the invention provides an organic semiconductor material comprising a compound of formula (I) as defined above.

In another aspect, the invention provides an organic semiconductor device comprising a layer of an organic semiconductor material, the organic semiconductor material comprising a compound of formula (I) as defined above.

In yet another aspect, the invention provides a method of forming an organic semiconductor device including the steps of providing a semiconductor substrate, and preparing a nanoparticle suspension of a compound of formula (I) as defined above in a solvent. An organic semiconductor layer is formed on the semiconductor substrate with the nanoparticle suspension.

Other objects, features, advantages and aspects of the present invention will become apparent to those skilled in the art from the following description and appended claims. It should be understood, however, that the following description, appended claims, and specific examples, while indicating preferred embodiments of the invention, are given by way of illustration only. Various changes and modifications within the spirit and scope of the disclosed invention will become readily apparent to those skilled in the art from reading the following.

DETAILED DESCRIPTION

Listed below are definitions of various terms used to describe the compounds of the present invention. These definitions apply to the terms as they are used throughout the specification unless they are otherwise limited in specific instances either individually or as part of a larger group.

The term "alkyl" as used herein refers to branched or straight chain hydrocarbon groups, comprising preferably 1 to 20 carbon atoms. Examples of alkyl groups include, but are not limited to, methyl, ethyl, n-propyl, isopropyl, n-butyl, isobutyl, t-butyl, pentyl, hexyl, 2-ethylhexyl, heptyl, nonyl, decyl, undecyl, dodecyl, tetradecyl, hexadecyl, octadecyl, t-octadecyl, etc. An alkyl group may be unsubstituted or optionally substituted with one or more substituents selected from halogen, lower alkyl, nitrile, and the like. Examples of substituted alkyl groups include, but are not limited to, haloalkyl groups such as $CF_3$, $CCl_3$, $CBr_3$, $CI_3$, $C_2F_5$, $C_3F_7$, $C_4H_9$, $C_5F_{11}$, $C_6H_{13}$, $C_7H_{15}$, $C_8H_{17}$, $C_9F_{19}$, $C_{10}F_{21}$, $C_{11}F_{23}$, $C_{12}F_{25}$, $C_{14}F_{29}$, $C_{16}F_{33}$, $CF_2CH_3$, $CF_2C_2H_5$, $CF_2C_3H_7$, $CF_2C_4H_9$, $CF_2C_5H_{11}$, $CF_2C_7H_{15}$, $CF_2C_{11}C_{23}$, $CCl_2C_{11}H_{23}$, $CBr_2C_{11}H_{23}$, $CI_2C_{11}H_{23}$, $CF_2C_{13}H_{27}$, $CF_2C_{15}H_{31}$, etc. or other substituted alkyl groups such as 2-methylhexyl, 2-ethylhexyl, 2-methyldodecyl, 2-ethyldodecyl, 3-ethyldoceyl, 4-ethyldocyl, 11-methyldodecyl, and the like.

The term "lower alkyl" as used herein refers to branched or straight chain alkyl groups comprising 1 to 6 carbon atoms, preferably 1 to 4 carbon atoms. Examples of lower alkyl groups include, but are not limited to, methyl, ethyl, n-propyl, i-propyl, n-butyl, i-butyl, sec-butyl, t-butyl, pentyl, and hexyl. A lower alkyl group may be unsubstituted or optionally substituted with one or more substituents including, but not limited to, substituents such as halogen, nitrile, $CF_3$, $CCl_3$, $CBr_3$, $CI_3$, $C_2F_5$, $C_3F_7$, $C_4H_9$, and the like.

The term "alkenyl" as used herein refers to branched or straight chain groups, comprising preferably 2 to 20 carbon atoms, and containing one or more double bonds. Examples of alkenyl groups include, but are not limited to, ethenyl, propenyl, butenyl, penentyl, hexenyl, heptenyl, nonenyl, decenyl, etc. An alkenyl group may be unsubstituted or optionally substituted with one or more substituents selected from halogen, nitrile, and the like.

The term "alkynyl" as used herein refers to branched or straight chain groups, comprising preferably 2 to 20 carbon atoms, and containing one or more triple bonds. Examples of alkynyl groups include, but are not limited to, ethynyl, propynyl, butynyl, penyntyl, hexynyl, heptynyl, nonynyl decynyl etc. An alkenyl group may be unsubstituted or optionally substituted with one or more substituents selected from halogen, nitrile, and the like.

The terms "lower alkenyl" and "lower alkynyl" have corresponding meanings to the term "lower alkyl" as defined above. Examples of lower alkenyl and lower alkynyl groups include, but are not limited to, ethenyl, propenyl, butenyl, ethynyl, propynyl and butynyl. A lower alkenyl or alkynyl group may be unsubstituted or optionally substituted with one or more substituents selected from halogen, nitrile, and the like.

The term "amine" or "amino" as used herein refers to a group containing —NH— or —NR—, wherein R may be an alkyl group as defined above such as, for example, methyl, ethyl, n-propyl, i-propyl, n-butyl, i-butyl, sec-butyl, t-butyl, pentyl, hexyl, and the like.

The term "carbonyl" as used herein refers to a group containing —(C=O)—.

The term "ester" as used herein refers to a group containing —(C=O)O— or —O(C=O)—.

The term "carbonate ester" as used herein refers to a group containing —O(C=O)O—.

The term "ether" as used herein refers to a group containing —O—.

The term "sulphide" as used herein refers to a group containing —S—.

The term "organosilane" as used herein refers to a group containing —SiR°R°°—, wherein R° and R°° may each independently of each other be H, a lower alkyl as defined above, or the like.

The term "thioate" as used herein refers to a group containing —S(C=O)— or —(C=O)—.

The term "halo" or "halogen" as used herein refers to F, Cl, Br or I.

The term "nitrile" as used herein refers to the group —C≡N.

The term "substituted" is intended to describe moieties having substituents replacing a hydrogen atom on one or more atoms, e.g. C, O or N, of a molecule.

As described herein above, the present invention relates to compounds of formula (I), to use of such compounds in semiconductor applications, and to methods for their preparation.

Preferred are the compounds of formula (I) wherein one or both of R1 and R2 have an atom length of from about 10 atoms to about 16 atoms, and more preferably an atom length of about 12 atoms.

Also preferred are the compounds of formula (I) wherein one or both of R1 and R2 independently comprise one or more of a group comprising: an alkyl, an alkenyl, an alkynyl, an amine, a carbonyl, an ester, a carbonate ester, an ether, a sulphide, an organosilane and a thioate.

Further preferred are the compounds of formula (I) wherein one or both of R1 and R2 comprise a straight chained alkyl.

Also preferred are the compounds of formula (I) wherein n is an integer from 4 to 20, inclusive.

Some examples of the compounds of formula (I) are shown by the following structural formulas, but the present invention is not limited to these embodiments.

(Ia)

(Ib)

(Ic)

(Id)

Compounds provided by the invention are hereinafter designated as "compound(s) of the invention".

It will be appreciated that the compounds of the invention may exist in the form of optical isomers, racemates or diastereoisomers. The scope of this invention embraces all stereochemically isomeric forms of the compounds. For example, although the compound of formula (I) is illustrated in an anti-syn conformation, it should be understood that the present invention embraces all other stereochemically isomeric forms of the compound of formula (I) including the anti-anti conformation illustrated below as an example:

(I')

The term "stereochemically isomeric forms" as used herein therefore means all possible isomeric forms which the compounds of the invention may possess. Unless otherwise mentioned or indicated, the chemical structures, systematic names and formulae of the compounds denote the mixture of all possible stereochemically isomeric forms, containing all diastereomers and enantiomers of the basic molecular structure. In particular, stereogenic centers may have the R- or S-configuration.

Compounds of the present invention are particularly useful when employed as semiconductors or charge transport materials in electronic devices such as organic field effect transistors (OFETs), organic light emitting diodes (OLEDs), and organic photovoltaic diodes. The compounds of the present invention when employed as the active semiconductor in an organic thin film transistor may be used, for example, in organic and plastic electronic devices including radio frequency identification devices (RFIDs), smart cards, driving circuits for liquid crystal displays, semi-conducting components-based displays, organic light emitting diodes (OLED) (including applications in both the charge transport and electroluminescent layers), photovoltaic or sensor devices, photoconductors, electrophotographic recording, organic memory devices, BIOFET sensors, as electrode materials in batteries, etc.

The performance of organic thin film transistor (OTFT) devices is principally based upon the charge carrier mobility of the semi-conducting material and the current on/off ratio. Accordingly, the ideal semiconductor should have low conductivity in the off state and high charge carrier mobility (i.e., greater than $1 \times 10^{-3}$ cm$^2$V$^{-1}$ s$^{-1}$). Additionally, it is important that the semi-conducting material is relatively stable to oxidation, that is, a high ionization potential, as oxidation leads to reduced device performance.

Organic semiconductor materials of the present invention are easily synthesized, have high charge carrier mobility and good processability. The organic semiconductor materials of the present invention may be processed to form thin, large area films for use in electronic devices. The organic semiconductor materials of the present invention are oxidatively stable, and have been shown to retain, and even improve, the desirable properties of semiconductor devices made therefrom. More particularly, the organic semiconductor materials of the present invention have been shown to afford excellent thin film transistor (TFT) performance (e.g. field effect mobility up to 0.3 cm$^2$V$^{-1}$ s$^{-1}$ and current on/off ratio greater than $1 \times 10^7$) under ambient conditions when used as the active layer in bottom-contact OTFTs via a solution-processed procedure. Further advantageously, no precautionary measures such as, for example, to exclude oxygen, moisture, or light, were required during device fabrication. In summary, the organic semiconductor materials of the present invention afford the following advantages: high charge carrier mobility; large current on/off ratio in air; good solution processability for low cost manufacturing; and high stability against polymer oxidation.

General Synthetic Methods

The compounds of the present invention may be prepared by the methods depicted in the reaction schemes shown below. The starting materials and reagents used in preparing these compounds are either available commercially or are prepared by methods known to those skilled in the art. These schemes are merely illustrative of some of the methods by which the compounds of this invention can be synthesized, and various modifications to these schemes can be made and will be suggested to one skilled in the art having referred to this disclosure.

SCHEME A: Preparation of 2,6-Bis-(3-alkyl-thiophen-2-yl)-dithieno[3,2-b; 2',3'-d]thiophene

Preparation of 2,6-Bis-(3-alkyl-thiophen-2-yl)-dithieno[3,2-b; 2',3'-d]thiophene may be fulfilled through Suzuki coupling reaction normally.

Step 1: 2,6-Dibromo-dithieno[3,2-b; 2',3'-d]thiophene [Frey, Joseph; Bond, Andrew D.; Holmes, Andrew B. Chem. Commun. 2002, 20, 2424-2425.] and 4,4,5,5-Tetramethyl-2-(3-dodecyl-thiophen-2-yl)-[1,3,2]dioxaborolane [Cremer, Jens; Mena-Osteritz, Elena; Pschierer, Neil G.; Muellen, Klaus; Baeuerle, Peter. Org. Biomol. Chem. 2005, 3(6), 985-995.] are prepared according to the respective published procedures.

Step 2: To a Schlenk flask is added 2,6-Dibromo-dithieno [3,2-b; 2',3'-d]thiophene (1 equivalent), 2-(3-dodecyl-thiophen-2-yl)-4,4,5,5-tetramethyl-[1,3,2]dioxaborolane (1.1 equivalents), potassium carbonate (10 equivalents), then the flask is evacuated and filled with nitrogen several times to remove traces of air. Pd(PPh$_3$)$_4$ (5% equivalents) is then added under the protection of nitrogen. THF/H$_2$O (volume ratio: 3/2) solution is bubbled with nitrogen for 15 mins, and added into the flask. The concentration of potassium carbonate in aqueous solution is 2M. The flask is securely sealed and stirred for 72 h at 95° C. The reaction mixture is cooled to room temperature. The organic layer is separated, diluted with hexane, and then washed with water. The pure product is obtained by separation through silica gel column chromatography with hexane as the eluent.

2,6-Bis-(3-dodecyl-thiophen-2-yl)-dithieno[3,2-b; 2',3'-d] thiophene: $^1$H-NMR (300 MHz, CDCl$_3$) d 7.25 (s, 2H), 7.22 (d, 2H), 6.96 (d, 2H), 2.80 (t, 4H), 1.67 (m, 4H), 1.24 (m, 36H), 0.88 (t, 6H). $^{13}$C-NMR (75 MHz, CDCl$_3$) d 140.9, 140.3, 136.9, 130.6, 130.5, 130.1, 124.4, 119.2, 31.9, 30.7, 29.7 (2C), 29.6 (2C), 29.5, 29.4, 29.3, 29.2, 22.7, 14.1.

SCHEME B: Preparation of poly(2,6-Bis-(3-alkyl-thiophen-2-yl)-dithieno[3,2-b; 2',3'-d]thiophene)

Poly(2,6-bis(3-dodecythiophen-2-yl)dithieno[3,2-b; 2',3'-d]thiophene) may be synthesized from its corresponding monomer, 2,6-Bis-(3-dodecyl-thiophen-2-yl)-dithieno[3,2-b; 2',3'-d]thiophene, by FeCl₃-mediated oxidative coupling polymerization in chlorobenzene.

Step 1: A slurry of iron (III) Chloride (2.0 mmol) and chlorobenzene (15 ml) is added through a 2-mm tube to a stirred solution of monomer (1.0 mmol) in chlorobenzene (15 ml). The polymer solution is stirred for 36 h at 50° C., while dry oxygen is bubbled through. The black mixture is washed with water to remove excess FeCl₃ to give a dark green-black mixture. This is stirred with 20 ml of conc. aqueous ammonia and chlorobenzene for 30 mins at room temperature to produce a purple-red chlorobenzene solution which is washed several times with water and dried over MgSO₄. Removal of the solvent at reduced pressure gives a dark purple solid. Purification by Soxhlet extraction with hexane and subsequent in vacuo drying affords the bulk polymer.

Poly(2,6-bis(3-dodecythiophen-2-yl)dithieno[3,2-b; 2',3'-d]thiophene): $^1$H-NMR (300 MHz, CDCl$_3$) d 7.32 (s, 2H), 7.05 (s, 2H), 2.79 (br, 4H), 1.69 (br, 4H), 1.26 (br, 36H), 0.87 (t, 6H).

SCHEME C: Preparation of poly(2,6-Bis-(3-alkyl-thiophen-2-yl)-dithieno[3,2-b; 2',3'-d]thiophene)

Poly(2,6-bis(3-dodecythiophen-2-yl)dithieno[3,2-b; 2',3'-d]thiophene) may alternatively be prepared through Stille coupling copolymerization between 2,6-Bis-trimethylstannanyl-dithieno[3,2-b; 2',3'-d]thiophene and 5,5'-Dibromo-4,4'-dialkyl-[2,2']bithiophene.

Step 1: 2,6-Bis-trimethylstannanyl-dithieno[3,2-b; 2',3'-d]thiophene [Frey, Joseph; Bond, Andrew D.; Holmes, Andrew B. Chem. Commun. 2002, 20, 2424-2425.] and 5,5'-Dibromo-4,4'-didodecyl-[2,2']bithiophene[Takahashi, Masabumi; Masui, Kentaro; Sekiguchi, Hiroki; Kobayashi, Nobuhiko; Mori, Atsunori; Funahashi, Masahiro; Tamaoki, Nobuyuki. J. Am. Chem. Soc. 2006, 128(33), 10930-10933.] are prepared according to the respective published procedures.

Step 2: To a Schlenk flask is added 2,6-Bis-trimethylstannanyl-dithieno[3,2-b; 2',3'-d]thiophene (1 equivalent), 5,5'-Dibromo-4,4'-didodecyl-[2,2']bithiophene (1 equivalent), tri (o-toyl) phosphine (8 mol % equivalent), tris (dibenzylideneacetone)dipalladium (2 mol % equivalent) and dry chlorobenzene (30 ml) under the protection of nitrogen. The flask is securely sealed and stirred for 48 h at 120° C. After cooling to room temperature, the reaction mixture is precipitated into a mixture of methanol (100 ml) and concentrated hydrochloric acid (4 ml) and stirred for 16 h. The precipitate is collected, extracted with methanol (Soxhlet) for 24 h, and dried under vacuum to afford the bulk product.

Figure 1:
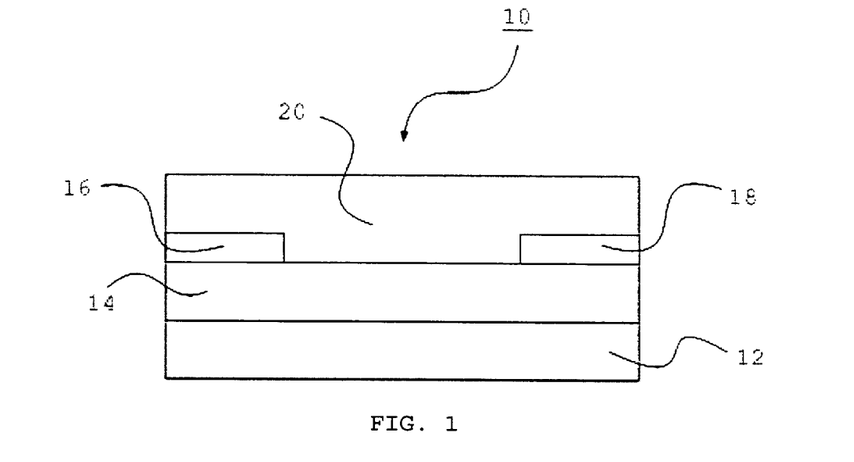
FIG. 1 is an enlarged cross-sectional view of an organic field effect transistor (OFET) in accordance with an embodiment of the present invention.

Referring now to FIG. 1, an enlarged cross-sectional view of an organic field effect transistor (OFET) 10 in accordance with an embodiment of the present invention is shown. The OFET 10 comprises a gate electrode 12, a gate dielectric layer 14 formed on the gate electrode 12, and a source electrode 16 and a drain electrode 18 formed on the gate dielectric layer 14. A layer 20 of an organic semiconductor material of the present invention is provided as a channel layer between the source electrode 16 and the drain electrode 18.

Figure 2:
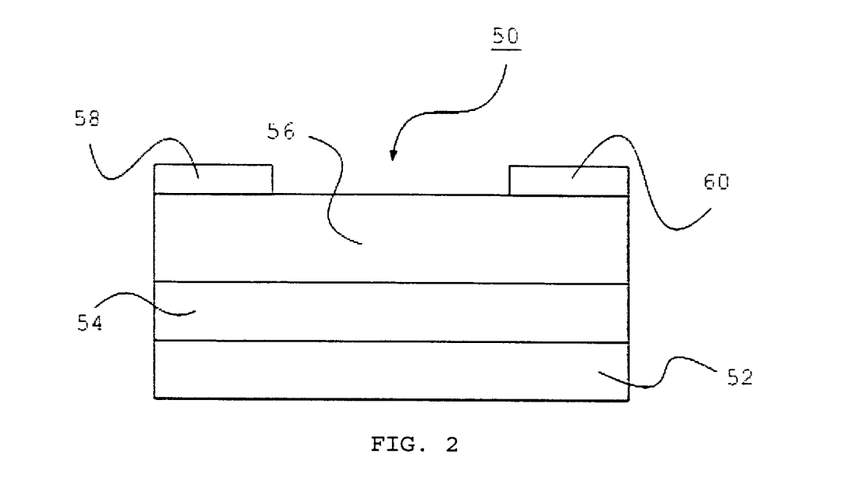
FIG. 2 is an enlarged cross-sectional view of an OFET in accordance with another embodiment of the present invention.

Referring now to FIG. 2, an enlarged cross-sectional view of an organic field effect transistor (OFET) 50 in accordance with another embodiment of the present invention is shown. The OFET 50 comprises a gate electrode 52 and a gate dielectric layer 54 formed on the gate electrode 52. A layer 56 of an organic semiconductor material of the present invention is formed on the gate dielectric layer 54 as a channel layer, and a source electrode 58 and a drain electrode 60 are formed on the organic semiconductor layer 56.

Figure 3:
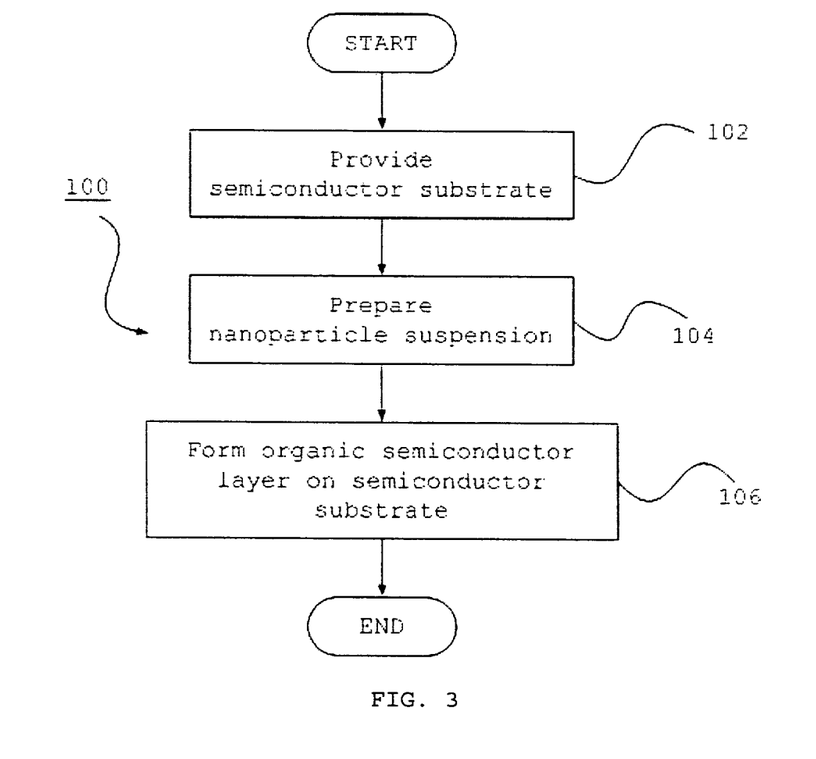
FIG. 3 is a flow diagram illustrating a method of forming an organic semiconductor device in accordance with an embodiment of the present invention.

Referring now to FIG. 3, a flow diagram illustrating a method 100 of forming an organic semiconductor device in accordance with an embodiment of the present invention is shown. The method 100 begins at step 102 with the provision of a semiconductor substrate. At step 104, a nanoparticle suspension of a compound of the present invention is prepared in a solvent of reduced toxicity such as, for example, an alkane having from about 6 to about 20 carbon atoms (e.g. hexane, heptane, octane, etc.), toluene or tetrahydrofuran (THF). The nanoparticle suspension may be prepared, in one embodiment, via an ultrasonication process. An organic semiconductor layer is formed on the semiconductor substrate with the nanoparticle suspension at step 106.

EXAMPLES

The invention is described with reference to the following examples. It is to be appreciated that the invention is not limited to these examples.

Example 1

Device Characteristics

Field effect transistor substrates were made using a heavily doped N-type silicon wafer as the common gate electrode and a 100 nm thermally oxidized SiO$_2$ layer as the gate dielectric. The gold source and drain electrodes were patterned in a bottom contact configuration using a conventional photolithography method. A 10 nm layer of titanium was used as an adhesion layer for the gold on SiO$_2$. The SiO$_2$ surface of the wafer substrate was first cleaned with Piranha solution (mixture of 70% sulfuric acid and 30% hydrogen peroxide) and then modified with organosilane by immersing the clean wafer in 10 mM hexane solution of octyltrichlorosilane (OTS-8) for 45 minutes at room temperature, thoroughly rinsing the substrate with hexane and 2-propanol then blowing dry with nitrogen gas. The gold source and drain electrodes were modified with octylthiol self-assembled monolayer to reduce the contact resistance. The substrate was immersed into 5 mM solution of octylthiol in ethanol for more than 24 hours, and then rinsed with ethanol before depositing the semiconductor layer.

For the purpose of confirming the device characteristics of an organic semiconductor material according to an embodiment of the present invention, a solution of poly(2,6-bis(3-dodecythiophen-2-yl)dithieno[3,2-b; 2',3'-d]thiophene) in anhydrous chlorobenzene (4 mg/ml) was deposited on the modified SiO$_2$ surface by drop-casting. The devices were annealed in a vacuum oven at 160° C. for 45 minutes and then slowly cooled to room temperature before evaluation. The substrate was patterned with a series of transistors with various channel lengths (L) from 20 μm to 100 μm and widths (W) from 3 mm to 16 mm.

Electrical properties of the transistors were characterized using a Cascade Microtech probe station and an Agilent E5270B 8-Slot Precision Measurement Mainframe at ambient conditions without taking any precautions to isolate the material and device from exposure to ambient oxygen, moisture, or light. The obtained results are shown in FIGS. 4 and 5.

Figure 4:
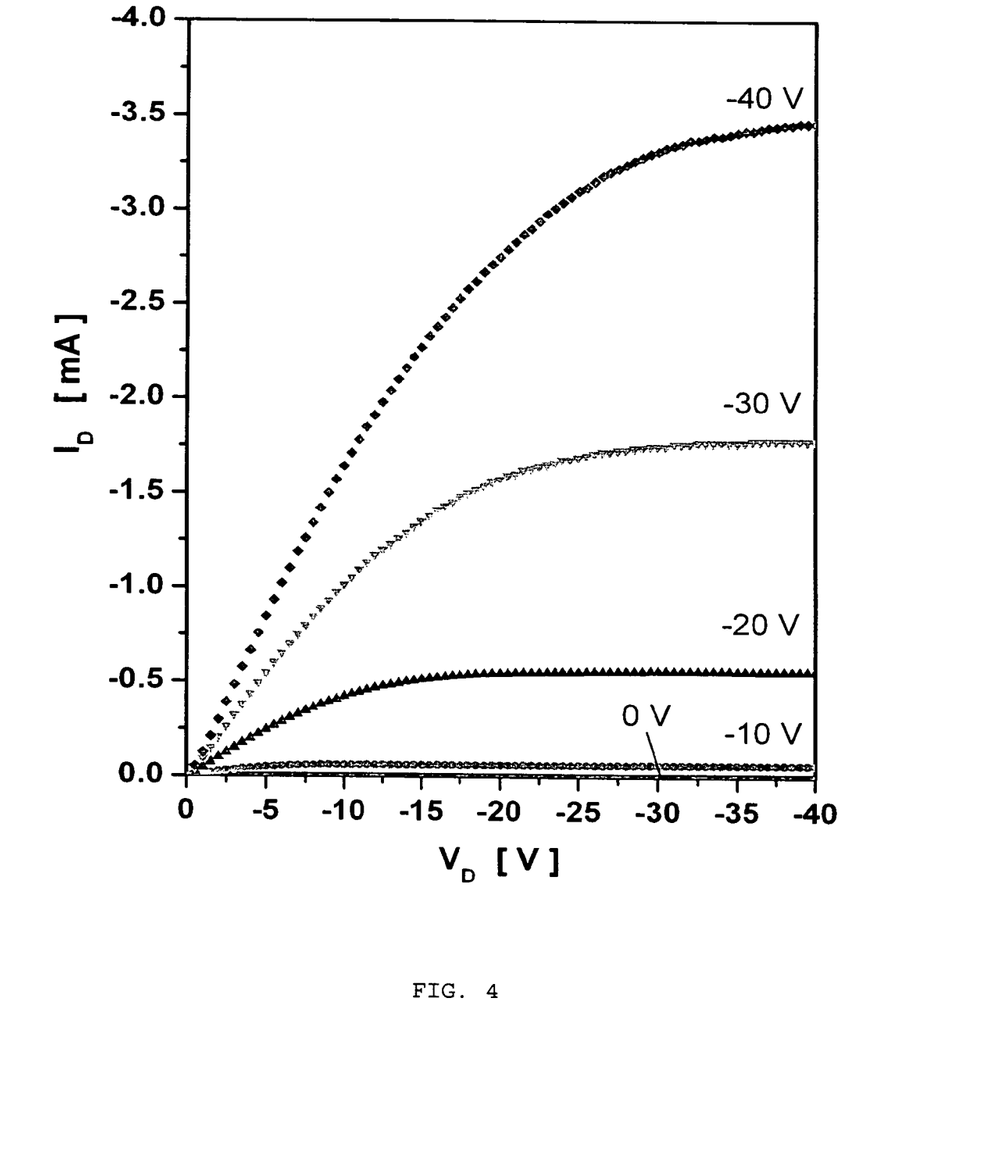
FIG. 4 is a graph showing a $V_D$-$I_D$ characteristic of an organic thin film transistor including, as a channel layer, a semiconductor thin film made of poly(2,6-bis(3-dodecylthiophen-2-yl)dithieno[3,2-b; 2',3'-d]thiophene) in accordance with an embodiment of the present invention.
Figure 5:
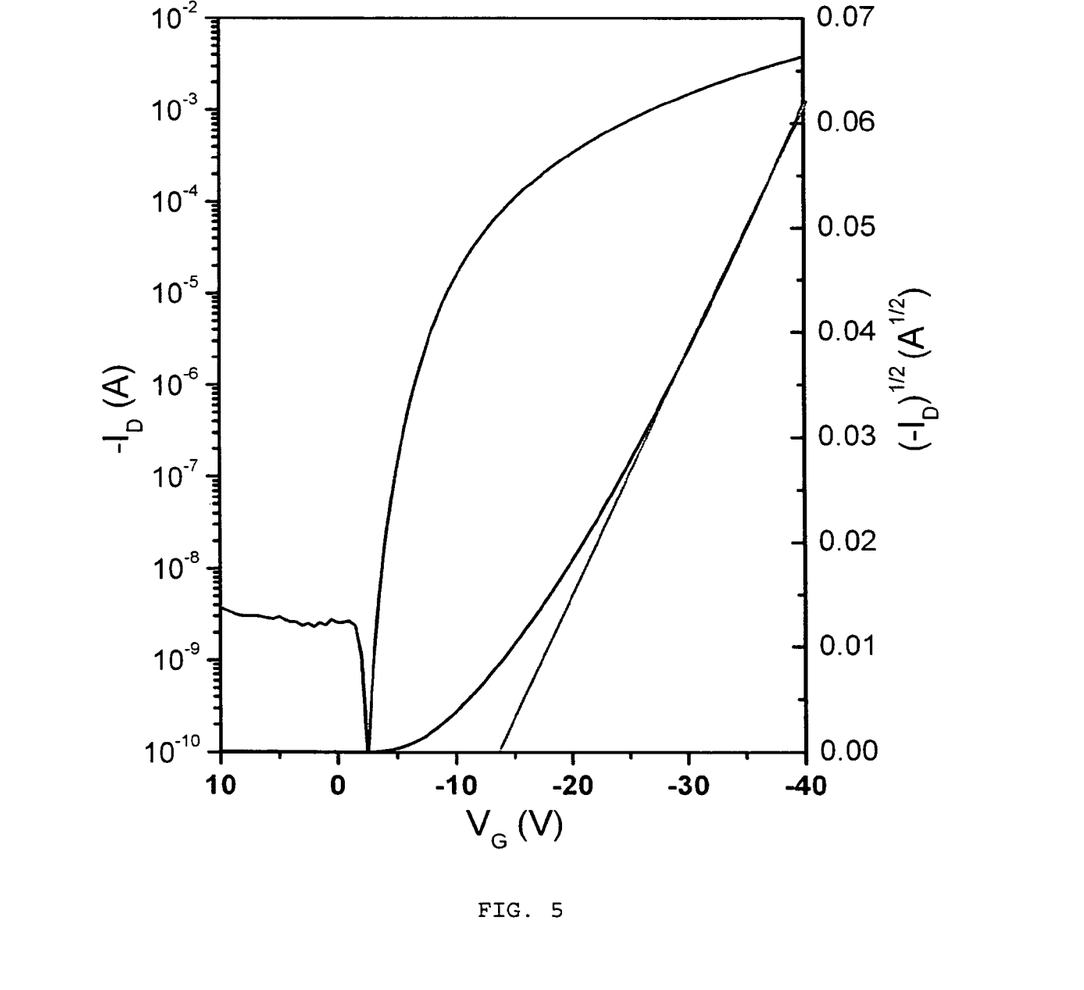
FIG. 5 is a graph showing a $V_G$-$I_D$ characteristic of an organic thin film transistor including, as a channel layer, a semiconductor thin film made of poly(2,6-bis(3-dodecylthiophen-2-yl)dithieno[3,2-b; 2',3'-d]thiophene) in accordance with an embodiment of the present invention.

The organic field effect transistor (OFET) mobility was computed from the saturation region of the I-V curves of FIG. 4 using the following equation (1):

$$I_{Dsat} = \frac{W}{2L} C_i \mu (v_g - V_{th})^2. \quad (1)$$

The calculations show that field effect mobility of up to 0.3 cm$^2$V$^{-1}$ s$^{-1}$ are attainable with poly(2,6-bis(3-dodecylthiophen-2-yl)dithieno[3,2-b; 2',3'-d]thiophene).

Further, as can be seen from FIG. 5, a current on/off ratio of greater than 1×10$^7$ is achievable with poly(2,6-bis(3-dodecylthiophen-2-yl)dithieno[3,2-b; 2',3'-d]thiophene).

It is concluded therefore that poly(2,6-bis(3-dodecylthiophen-2-yl)dithieno[3,2-b; 2',3'-d]thiophene) affords excellent thin film transistor (TFT) performance (field effect mobility of up to 0.3 cm$^2$V$^{-1}$ s$^{-1}$ and current on/off ratio above 1×10$^7$) under ambient conditions when used as the active layer in a bottom-contact organic thin film transistor (OTFT) formed through a solution-processed procedure, in particular, using chlorobenzene as the solvent. Further advantageously, no precautionary measures to exclude oxygen, moisture, or light are required during device fabrication.

Example 2

Solution Processability

Ultrasonication of poly(2,6-bis(3-dodecythiophen-2-yl)dithieno[3,2-b; 2',3'-d]thiophene) in an alkane having from about 6 to about 20 carbon atoms (e.g. hexane, heptane, octane, etc.), toluene, or THF for one hour was found to result in the formation of a purplish suspension of polymer nanoparticles.

The field effect transistor (FET) properties of the polymer nanoparticles were characterized using a bottom-gate, bottom-contact thin film transistor (TFT) device configuration. The TFTs were built on an n-doped silicon wafer with an octyltrichlorosilane-modified SiO$_2$-gate dielectric and octanethiol-modified gold source/drain electrodes, the fabrication of which is described above in Example 1. A nanoparticle suspension of poly(2,6-bis(3-dodecythiophen-2-yl)dithieno[3,2-b; 2',3'-d]thiophene) in hexane is prepared by agitating a mixture of poly(2,6-bis(3-dodecythiophen-2-yl)dithieno[3,2-b; 2$^{1,3'}$-d]thiophene) and hexane (4 mg/ml) in a vial in an ultrasonic bath at room temperature for 1 hour. The suspension of the polymer nanoparticles in hexane (4 mg/ml) is then drop-deposited into the TFT channels of the above devices and dried in an oven. The processing of the organic thin film transistor (OTFT) devices are carried out under ambient conditions without taking precautionary measures to isolate the material and devices from exposure to ambient oxygen, moisture, or light.

Figure 6:
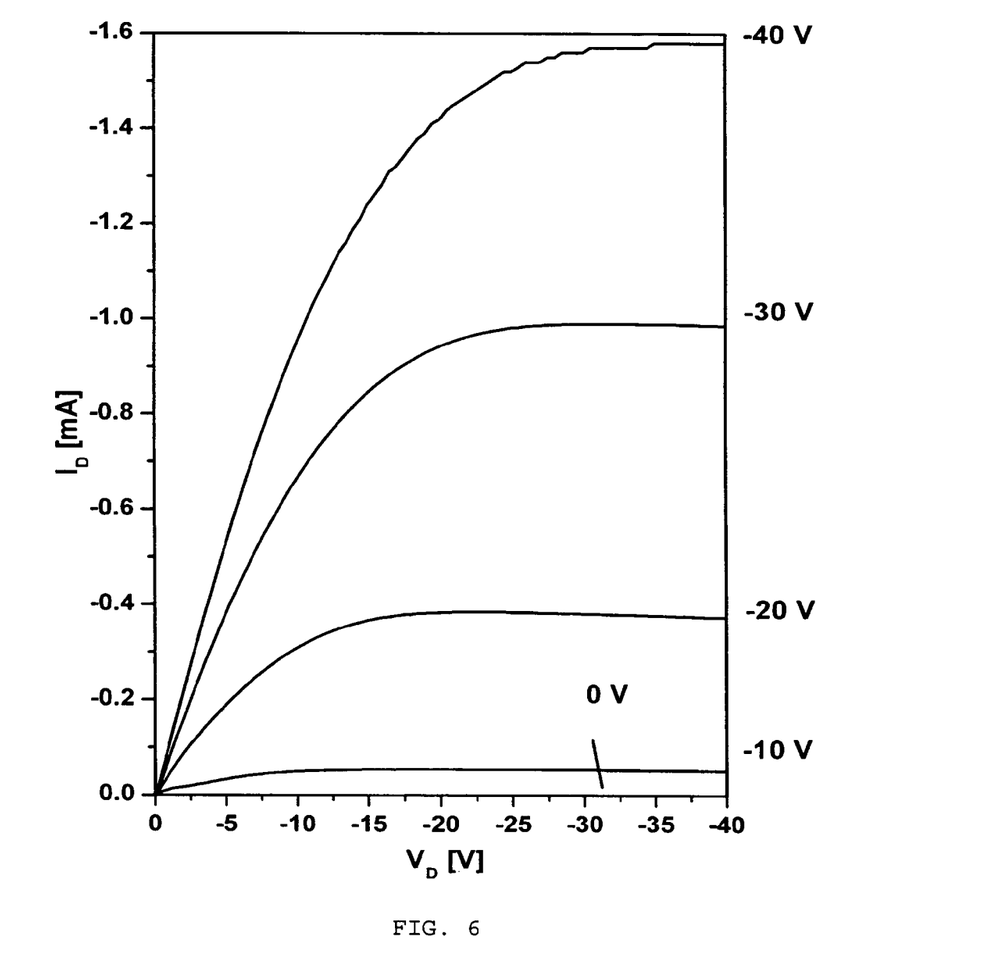
FIG. 6 is a graph showing a $V_D$-$I_D$ characteristic of an organic thin film transistor including, as a channel layer, a semiconductor thin film made from a nanoparticle suspension of poly(2,6-bis(3-dodecylthiophen-2-yl)dithieno[3,2-b; 2',3'-d]thiophene) in hexane in accordance with an embodiment of the present invention.
Figure 7:
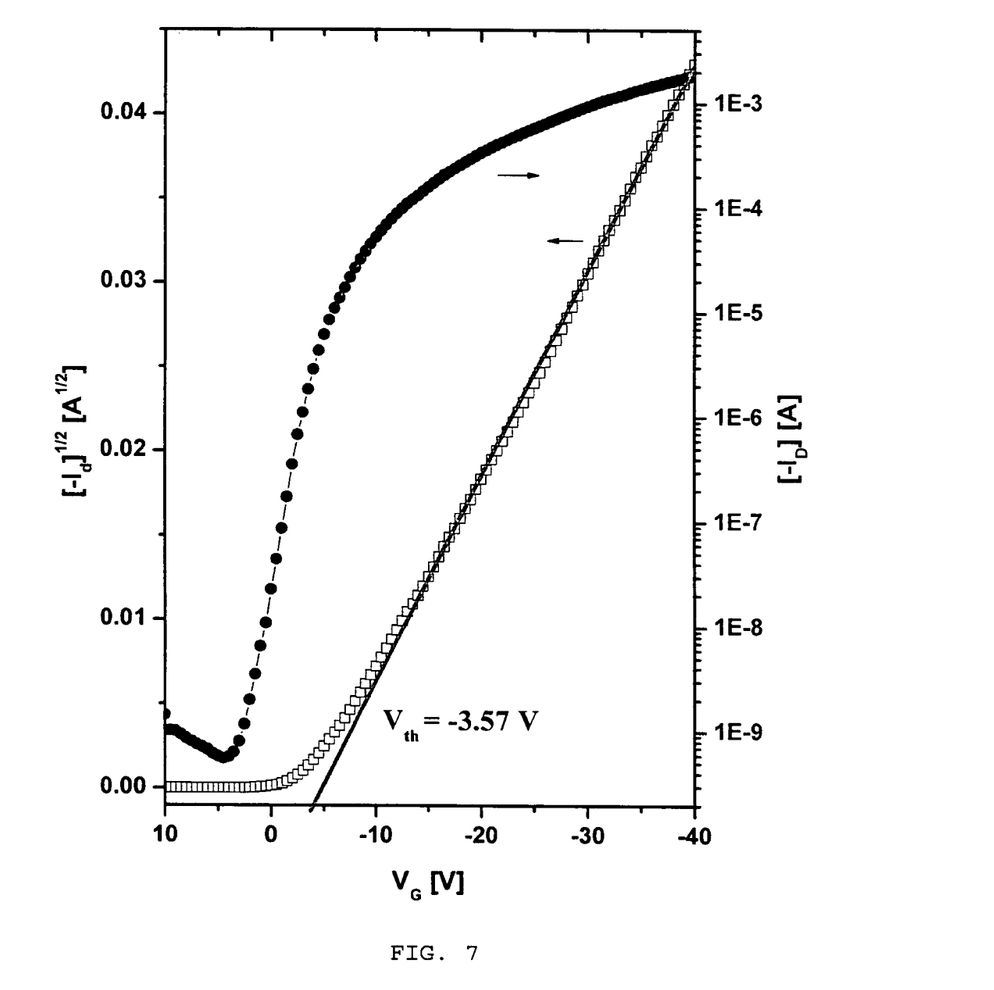
FIG. 7 is a graph showing a $V_G$-$I_D$ characteristic of an organic thin film transistor including, as a channel layer, a semiconductor thin film made from a nanoparticle suspension of poly(2,6-bis(3-dodecylthiophen-2-yl)dithieno[3,2-b; 2',3'-d]thiophene) in hexane in accordance with an embodiment of the present invention.

Electrical properties of the transistors were characterized using similar methods as were described in Example 1 and the obtained results are shown in FIGS. 6 and 7.

The organic field effect transistor (OFET) mobility was computed from the saturation region of the I-V curves of FIG. 6 using equation (1) given above.

As prepared, the TFTs show a FET mobility of 4.2×10$^{-3}$ cm$^2$ V$^{-1}$ s$^{-1}$ and an on/off ratio of 10$^3$. After thermal annealing at 160° C., the devices exhibited significant improvements in both mobility and on/off ratio. In particular, these values increased to 0.16 cm$^2$ V$^{-1}$ s$^{-1}$ and 10$^6$, respectively.

These results are comparable to the performance of the OTFT devices fabricated from a chlorobenzene solution described above in Example 1. This represents a first report of high-mobility polymer OTFTs fabricated from an environmentally benign solvent (hexane) under ambient conditions, in contrast to most high-mobility polymer semiconductors which require toxic chlorinated benzene solvents for fabrication.

The description of the preferred embodiments of the present invention has been presented for purposes of illustration and description, but is not intended to be exhaustive or to limit the invention to the forms disclosed. It will be appreciated by those skilled in the art that changes could be made to the embodiments described above without departing from the broad inventive concept thereof. It is understood, therefore, that this invention is not limited to the particular embodiments disclosed, but covers modifications within the spirit and scope of the present invention as defined by the appended claims.

ABBREVIATIONS

Me$_3$Sn=trimethyltin
Pd(Ph$_3$P)$_4$=tetrakis(triphenylphosphine)palladium
Pd$_2$(dbda)$_3$=tris(dibenzylideneacetone)dipalladium
THF=tetrahydrofuran

The invention claimed is:

1. A compound of formula (I):

wherein
n is an integer from 1 to 500, inclusive;
and R1 and R2 are each independently a moiety having an atom length of from about 8 atoms to about 20 atoms.

2. The compound of claim 1, wherein one or both of R1 and R2 have an atom length of from about 10 atoms to about 16 atoms.

3. The compound of claim 2, wherein one or both of R1 and R2 have an atom length of about 12 atoms.

4. The compound of claim 1, wherein one or both of R1 and R2 independently comprise one or more of a group comprising: an alkyl, an alkenyl, an alkynyl, an amine, a carbonyl, an ester, a carbonate ester, an ether, a sulphide, an organosilane and a thioate.

5. The compound of claim 4, wherein one or both of R1 and R2 comprise a straight chained alkyl.

6. The compound of claim 5, wherein both R1 and R2 are dodecyl.

7. The compound of claim 1, wherein n is an integer from 4 to 40, inclusive.

8. An organic semiconductor material comprising a compound of claim 1.

9. An organic semiconductor device comprising a layer of an organic semiconductor material of claim 8.

10. A method of forming an organic semiconductor device, comprising:
providing a semiconductor substrate;
preparing a nanoparticle suspension of a compound of claim 1 in a solvent;
and forming an organic semiconductor layer on the semiconductor substrate with the nanoparticle suspension.

11. The method of forming an organic semiconductor device of claim 10, wherein the nanoparticle suspension is prepared via an ultrasonication process.

12. The method of forming an organic semiconductor device of claim 10, wherein the solvent is one of an alkane having from about 6 to about 20 carbon atoms, toluene and tetrahydrofuran (THF).

* * * * *